(12) United States Patent
Guenkel et al.

(10) Patent No.: US 9,139,509 B2
(45) Date of Patent: Sep. 22, 2015

(54) REMOVAL OF NON-AROMATIC IMPURITIES FROM A NITRATION PROCESS

(75) Inventors: Alfred A. Guenkel, Vancouver (CA); Sergio Berretta, Vancouver (CA)

(73) Assignee: NORAM INTERNATIONAL LIMITED, Dublin (IE)

( * ) Notice: Subject to any disclaimer, the term of this patent is extended or adjusted under 35 U.S.C. 154(b) by 351 days.

(21) Appl. No.: 13/636,478

(22) PCT Filed: Feb. 17, 2011

(86) PCT No.: PCT/IB2011/000306
§ 371 (c)(1), (2), (4) Date: Sep. 21, 2012

(87) PCT Pub. No.: WO2012/110839
PCT Pub. Date: Aug. 23, 2012

(65) Prior Publication Data
US 2013/0018210 A1    Jan. 17, 2013

(51) Int. Cl.
*C07C 205/00* (2006.01)
*C07B 41/00* (2006.01)
*C07C 201/16* (2006.01)

(52) U.S. Cl.
CPC .................................. *C07C 201/16* (2013.01)

(58) Field of Classification Search
CPC ............................ C07C 205/06; C07C 201/06
USPC ........................................ 568/939, 940, 950
See application file for complete search history.

(56) References Cited

U.S. PATENT DOCUMENTS

| | | | |
|---|---|---|---|
| 3,780,116 A | 12/1973 | Sahgal | |
| 4,363,704 A | 12/1982 | Berg | |
| 4,514,262 A | 4/1985 | Berg | |
| 5,313,009 A | 5/1994 | Guenkel et al. | |
| 5,648,565 A | 7/1997 | Konig et al. | |
| 6,586,645 B2 | 7/2003 | Demuth et al. | |

FOREIGN PATENT DOCUMENTS

WO    9211227 A1    7/1992

OTHER PUBLICATIONS

International Search Report, completed Jan. 2, 2012 and mailed Jan. 11, 2012; Applicant: Noram International Limited, Application No. PCT/IB2011/000306 filed Feb. 17, 2011 (8 pages).

*Primary Examiner* — Jafar Parsa
(74) *Attorney, Agent, or Firm* — McKee, Voorhees & Sease, PLC

(57) ABSTRACT

A method and apparatus for removing non-aromatic impurities from non-nitrated aromatic reactant in a nitration production process, in which process an aromatic reactant is nitrated (100) to produce a nitrated aromatic product using a molar excess of the aromatic reactant, and non-nitrated aromatic reactant is recovered (102) from the produced nitrated aromatic product and is recycled (104) for use in the nitration production process. A portion of the removed excess non-nitrated aromatic reactant is diverted (106) and subjected to nitration (108). The nitrated stream may be further processed by separating out the spent acids (110) and the non-aromatic impurities (116). These streams may be sent (114, 118) to a suitable location in the nitration production train.

20 Claims, 2 Drawing Sheets

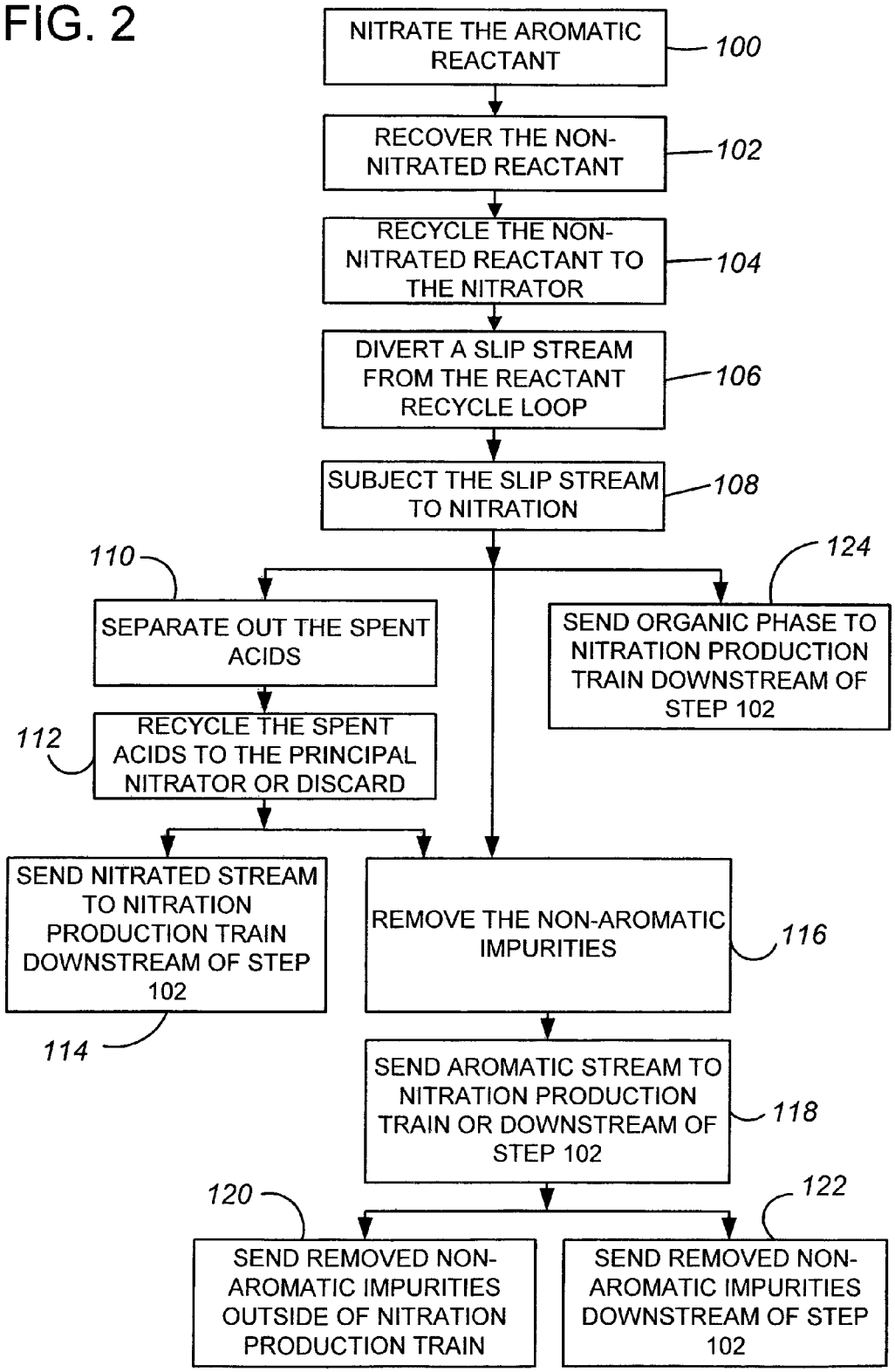

REMOVAL OF NON-AROMATIC IMPURITIES FROM A NITRATION PROCESS

CROSS-REFERENCE TO RELATED APPLICATIONS

This is a National Phase application claiming priority to PCT/IB2011/000306 filed Feb. 17, 2011, which is herein incorporated by reference in its entirety.

FIELD OF THE INVENTION

The invention pertains to the industrial production of nitrated aromatic compounds, and in particular to the removal of non-aromatic impurities during the production process.

BACKGROUND OF THE INVENTION

Nitrated aromatic hydrocarbons, such as nitrobenzene and nitrotoluene, are important chemical intermediates. Industrially, some nitration reactions are carried out with a molar excess of nitric acid over the aromatic compound, but others, for example the reaction of benzene and nitric acid to make nitrobenzene, operate with a molar excess of the aromatic compound. Examples in the patent literature of nitration processes for the production of nitroaromatic compounds where the nitration reaction is preferably carried out with a molar excess of the aromatic compound are Guenkel et al., U.S. Pat. No. 5,313,009 (e.g. production of mononitrobenzene); Konig et al., U.S. Pat. No. 5,648,565 (production of mononitrotoluene); and Demuth et al., U.S. Pat. No. 6,586,645 (production of nitrochlorobenzene).

Industrial applications of nitration reactions which operate with a molar excess of the aromatic compound would normally include a step for the recovery and recycling of the excess aromatic compound used (referred to herein as the 'excess aromatic recovery' step). This is the accepted industrial norm in the production of nitrobenzene, where a distillation column or live-steam stripper is used to recover the excess benzene from the produced nitrobenzene (typically, the excess aromatic compound is miscible in the produced nitrated product). The recovered excess benzene would normally contain some nitrobenzene.

Industrially, the aromatic compound to be nitrated will contain small quantities of non-aromatic compounds as impurities. In the case of benzene, examples of non-aromatic impurities include cyclohexane, methyl-cyclohexane, and ethyl-cyclopentane. The concentrations of these non-aromatic impurities will vary depending on the source of the aromatic compound. Many of these impurities do not nitrate and may degrade slowly in the nitration process, and, because of their organic nature, they mix with the produced nitrated product. Reference herein to 'non-aromatic impurities' means those non-aromatic impurities that do not nitrate in the nitration production train. A common physical attribute of these non-aromatic impurities is that they have boiling points close to that of the aromatic compound fed to the nitration reactor, or boiling points that lie somewhere between the boiling points of the nitrated product and the aromatic reactant. For example, benzene and cyclohexane have boiling points of 80° C. and 81° C. respectively, while the mononitrated product (mononitrobenzene) has a boiling point of 210° C. Table 1 lists non-aromatic impurities introduced by the benzene feed into a nitrobenzene plant known to the inventors and present in the recovered and recycled benzene stream of the same plant. Many of them have boiling points close to that of benzene or between the boiling points of benzene and mononitrobenzene.

TABLE 1

| Compound | Normal Boiling Point (° C.) | Compound | Normal Boiling Point (° C.) |
|---|---|---|---|
| 2-methy-butane | 28 | cyclohexane | 81 |
| pentane | 36 | 2,3-dimethyl-pentane | 90 |
| 2,2-dimethyl-butane | 50 | 3-methyl-hexane | 92 |
| cyclopentane | 49 | heptane | 98 |
| 3-methyl-pentane | 63 | Methyl-cyclohexane | 101 |
| hexane | 69 | Ethyl-cyclopentane | 104 |
| 2,2-dimethyl-pentane | 79 | 2,4-dimethyl-hexane | 109 |
| 2,4-dimethyl-pentane | 80 | Methylene-cyclohexane | 103 |
| 2,2,3-trimethyl-butane | 81 | 2,3-dimethyl-hexane | 116 |

As a result, a portion of the non-aromatic impurities is removed from the nitrated product in the excess aromatic recovery step (either distillation or live-steam stripping). Once removed from the nitrated product, these non-aromatic impurities mix with the recovered (excess) aromatic compound and are recycled back to the nitration reactor. Hence, the process naturally forms a closed loop where some non-aromatic impurities tend to build up. In general, the non-aromatic impurities building up in the process will be at their highest concentrations in the recovered and recycled aromatic stream. Once the recycled stream is introduced back into the reaction area, or back to storage, the non-aromatic impurities are diluted by the bulk of fresh aromatic compound addition.

In some cases, the build-up of these non-aromatic impurities can reach levels at which plant operation can be disrupted. Predicting whether build-up will disrupt production is very difficult. Some non-aromatics tend to degrade with time in the process. Once they degrade, their physical properties (e.g. vapor pressure, or acid solubility) change, giving the compounds a chance to naturally purge from the process. As a result, variables such as the types and concentrations of species of non-aromatic impurities and plant operating conditions play a role in whether build-ups will be sufficiently high to disrupt production or not.

The typical industrial method for removing non-aromatic impurities from a nitration plant to prevent build-up of the non-aromatic impurities from disrupting production is by purging. For example, the inventors are familiar with a nitrobenzene production facility where the build-up of non-aromatic impurities must be dealt with by having periodic purges of recycled benzene. Depending on the purge rate required, the loss of benzene and its disposal can be costly. Table 2 shows data for the concentration of non-aromatic impurities at different points in the process of that nitrobenzene production facility. These impurities, which amount to 330 ppm in the commercial benzene supplied to the plant, can build up by a factor of 45 in the feed to the nitration reactors and by a factor of over 500 in the recovered and recycled benzene.

TABLE 2

| Location of measurement | Total Non-Aromatic Impurity Concentration (wt %) |
|---|---|
| Benzene From Storage | 0.033 |
| Benzene To Reactor (after benzene from storage and recycled | 1.5 |

TABLE 2-continued

| Location of measurement | Total Non-Aromatic Impurity Concentration (wt %) |
|---|---|
| benzene are mixed) | |
| Recovered and Recycled Benzene | 17.7 |

Where a purge of the excess aromatic reactant is used to reduce the build-up of non-aromatic impurities, the purged stream would typically be sent for disposal. Mixing of the purged stream into the final nitrated product is typically not an option as this would affect the product quality, specifically in respect of the concentration of the residual non-nitrated aromatic compound. In the case of nitrobenzene production, this approach would lead to a product nitrobenzene with a benzene content that would exceed normally acceptable commercial specifications.

In a different industry, namely petroleum refining, there are processes for the removal of non-aromatics from aromatic streams by means of extractive distillation. Examples of these processes are described in Berg, U.S. Pat. No. 4,363,704 and U.S. Pat. No. 4,514,262. Extractive distillation differs from conventional distillation in that a solvent is added to increase the volatility ratio between the aromatic and non-aromatic compounds. In general, the further the relative volatility is from unity, the easier the separation is when using stripping or distillation. Removal of non-aromatics through extractive distillation is complex, usually involving more than one distillation tower to remove both heavy and light impurities, or a single tall distillation column with multiple draws. Typically, some of the solvent ends up with the aromatic compound, which depending on the solvent may become an operational nuisance for the end user. The extractive distillation process is therefore not an attractive option for removing non-aromatic impurities in a nitration process.

There is a need for a cost-effective method and apparatus for the removal of non-aromatic impurities from the recovered and recycled excess aromatic reactant from a nitration process.

SUMMARY OF THE INVENTION

The invention provides a method and apparatus for the removal of non-aromatic impurities from the stream generated when the molar excess of the aromatic reactant used in the nitration process is recovered and recycled. The inventors have determined that such removal can be done, and build-up of non-aromatic impurities controlled, by diverting a portion of the recovered excess unreacted aromatic reactant and subjecting it to nitration, then further processing the nitrated stream and sending it to a suitable location in the nitration production train.

One aspect of the invention provides a method of removing non-aromatic impurities from non-nitrated aromatic reactant in a nitration production process, in which production process an aromatic reactant is nitrated to produce a nitrated aromatic product using a molar excess of the aromatic reactant, and non-nitrated aromatic reactant is recovered from the produced nitrated aromatic product and is recycled for use in the nitration production process, the method comprising the steps of diverting a portion of the recovered, non-nitrated aromatic reactant to form a stream comprising non-nitrated aromatic reactant with non-aromatic impurities, and subjecting the formed stream to nitration to produce a stream comprising nitrated aromatic product and non-aromatic compounds.

Another aspect of the invention provides an apparatus for removing non-aromatic impurities from non-nitrated aromatic reactant in a nitration production train, the production train having a nitration reactor for producing nitrated aromatic product using a molar excess of the aromatic reactant, a separation unit for recovering non-nitrated aromatic reactant from the produced nitrated aromatic product, and a recycling loop for recycling the recovered non-nitrated aromatic reactant from the extraction unit to the nitration reactor, the apparatus comprising means for diverting a portion of the recovered non-nitrated aromatic reactant to form a stream comprising non-nitrated aromatic reactant with non-aromatic impurities, and a secondary nitrator for receiving the formed stream and nitrating the non-nitrated aromatic reactant therein to produce a stream comprising nitrated aromatic product and non-aromatic impurities.

Further aspects of the invention and features of specific embodiments are described below.

BRIEF DESCRIPTION OF THE DRAWINGS

FIG. 2 is a flow chart showing the method of the invention.

DETAILED DESCRIPTION

Embodiments of the invention are described below in the context of the nitration of benzene to produce mononitrobenzene. However, it will be understood that this reaction is only one example of a nitration reaction in which a molar excess of the aromatic reactant is used, and the invention applies to all such nitration reactions. Examples of other such reactions are the nitration of toluene to produce mononitrotoluene, of chlorobenzene to produce mononitrochlorobenzene, and of mononitrotoluene to produce dinitrotoluene.

Figure 1A:
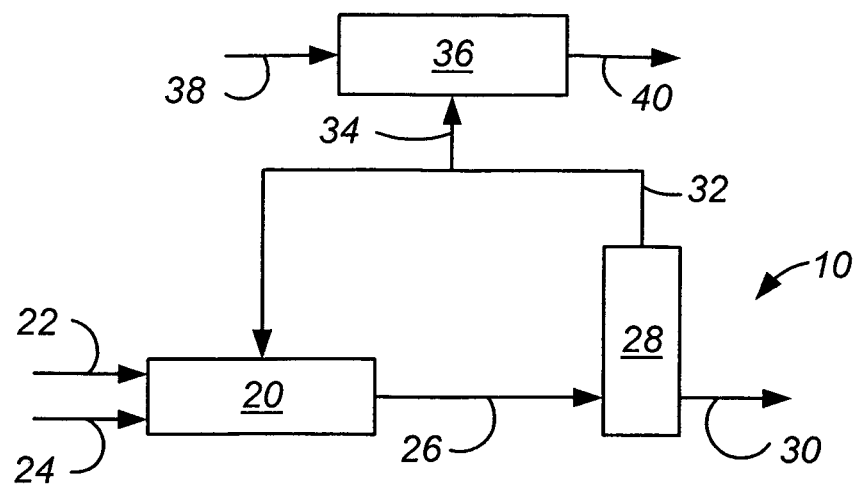
FIG. 1A is a schematic diagram of an embodiment of the invention, in which a slip stream of non-nitrated aromatic compound, with non-aromatic impurities, is subjected to nitration.

Referring first to FIG. 1A, a nitration production train 10 has a nitration reactor 20 which receives a stream 22 of benzene and a stream 24 of mixed acid (nitric and sulfuric acids, with water) and produces a stream of nitrobenzene 26, which also contains the non-aromatic compounds and reaction excess benzene. Alternatively, the acids (nitric acid and sulfuric acid) of stream 24 can be introduced into the reactor as separate streams. The nitration step may include washing and other unit operations (not illustrated in the drawing), in addition to the nitration reaction.

The nitrated product stream 26 is fed to a separation unit 28 of the nitration production train, for example a distillation column or steam stripper, to remove the excess, non-nitrated benzene. Product mononitrobenzene (stream 30) is removed from the bottom of the separation unit and may be sent to storage. A stream 32 of the excess non-nitrated benzene forms a recycle loop of the nitration production train and is recycled from the separation unit 28 to the nitration reactor 20. The stream 32 contains the non-aromatic impurities with a boiling point between that of benzene and mononitrobenzene, or lower than that of benzene. The stream 32 will also contain some mononitrobenzene.

A slip stream 34 is diverted from the excess benzene recycle stream 32 and is fed to a nitrator 36, referred to herein as the secondary nitrator (as distinguished from the principal nitration reactor 20 of the nitration production train). Alternatively, the entire excess benzene recycle stream (rather than only a slip stream) may be diverted to the secondary nitrator. The slip stream 34 may be taken on a continuous or non-continuous basis, as the method of the invention may be operated on a continuous or batch basis. The slip stream 34 may divert, for example, approximately 5% by volume of the recycle stream 32. A stream 38 of mixed acids (nitric and sulfuric) is introduced into the secondary nitrator 36. Alternatively, the two acids may be introduced separately into the secondary nitrator, or the acid stream may be mixed with the slip stream 34 prior to entering the secondary nitrator. The nitric and sulfuric acids may originate from the nitration production train or be provided from elsewhere. In the secondary nitrator, the benzene from the slip stream 34 is nitrated to produce mononitrobenzene. The stream 40 leaving the secondary nitrator comprises the produced mononitrobenzene, the non-aromatic impurities that were in the slip stream 34, and any non-nitrated benzene, plus the spent acids.

Figure 1B:
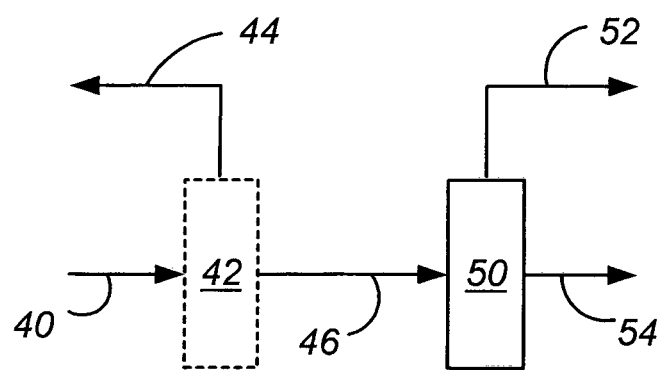
FIG. 1B is a schematic diagram of an embodiment of the invention, in which the stream leaving the secondary nitrator is subjected to further treatment or is conveyed to the nitration production train.

There are several options for dealing with this nitrated stream 40. The stream may be processed as illustrated in FIG. 1B. In one embodiment, the stream 40 is sent to a decanter 42 which separates the aqueous, acid phase (stream 44) containing the spent acids, from the organic phase (stream 46) containing the mononitrobenzene produced in the secondary nitrator 36, the non-aromatic impurities and any residual non-nitrated benzene. The decanter 42 is optional, as indicated by broken lines in FIG. 1B, because the separation may instead be done within the secondary nitrator 36 itself, in which case the acid phase stream 44 would exit directly from the secondary nitrator and the decanter 42 as a separate vessel would not be required. The acid phase may be recycled back to the nitration production train, i.e. to the nitration reactor 20, or be disposed of. By virtue of the nitration, the organic stream 46 has been substantially changed in composition relative to the recycle stream 32 and slip stream 34. It previously comprised an aromatic compound and non-aromatic impurities with similar boiling points. It now comprises a nitrated product and non-aromatic impurities having very different boiling points. In the present example of nitrobenzene production, the recovered and recycled stream 32 comprises benzene and non-aromatic impurities such as cyclohexane, both of which have similar boiling points. However, the nitrated stream 46 comprises mainly nitrobenzene and the same non-aromatic impurities, which have very different boiling points. Therefore, the separation of the non-aromatic impurities from the nitrated stream 46, using for example stripping or distillation, can be readily achieved. Table 3 presents the relative volatility of selected non-aromatic impurities from Table 1 relative to benzene at the normal boiling point of benzene. Table 4 presents the relative volatility of the same non-aromatic compounds relative to nitrobenzene at the normal boiling point of nitrobenzene.

TABLE 3

| Compound | Relative Volatility |
| --- | --- |
| Pentane/Benzene | 5.9 |
| Cyclopentane/Benzene | 2.6 |
| Hexane/Benzene | 2.3 |
| Heptane/Benzene | 0.9 |
| Cyclohexane/Benzene | 1.0 |
| 2,2,3-trimethyl-butane/Benzene | 1.5 |

TABLE 4

| Compound | Relative Volatility |
| --- | --- |
| Pentane/nitrobenzene | 36.1 |
| Cyclopentane/nitrobenzene | 23.8 |
| Hexane/nitrobenzene | 22.3 |
| Heptane/nitrobenzene | 14.1 |
| Cyclohexane/nitrobenzene | 13.6 |
| 2,2,3-trimethyl-butane/nitrobenzene | 16.6 |

In general, the relative volatility among compounds has a large impact on the number of theoretical plates required in a distillation column for a specific separation. For example, Berg, U.S. Pat. No. 4,363,704, shows that the number of theoretical plates required to separate toluene from methylcyclohexane, for a 99% purity, is 227 when the relative volatility is 1.5 but only 54 plates when the relative volatility is 5.5. This shows the advantage of increasing the relative volatility between compounds when separating non-aromatic impurities, which in the present invention is achieved by nitrating the aromatic component of the mixture.

The nitrated organic stream 46 is accordingly fed to a separation unit 50, referred to herein as a secondary separation unit to distinguish it from the principal separation unit 28 of the nitration production train. The secondary separation unit 50 may, for example, be a distillation column or a live-steam stripper. The non-aromatic impurities are removed, producing a stream 54 of mononitrobenzene. This stream 54 may be sent to any location within or downstream of the nitration production train. For example, stream 54 may be sent to the washing area of the nitration production train to remove residual acid from the mononitrobenzene.

The stream 52 of removed non-aromatic impurities from the secondary separation unit 50 may be disposed of elsewhere or blended with the nitration product downstream of the separation unit 28 (or at the bottom of the separation unit, provided that the stream is not materially subjected to separation), if the product specification allows to do so. This blending option is of important significance because it means that the non-aromatic impurities, stream 52, can now be mixed with the nitration product, stream 30, as a disposal route, without affecting the quality of the nitrated product in regards to the non-nitrated aromatic residual specie. In the case of the nitrobenzene, it means that the non-aromatic impurities stream 52 can be mixed with the nitrobenzene product, stream 30, without significantly affecting the specification of the nitrobenzene in regard to residual benzene concentration.

In some embodiments, the nitrated stream 40 is mixed, with or without further treatment (i.e. with or without one or both of the separation out of spent acids and the separation of the non-aromatic impurities), with the nitrated product in the nitration production train at any point downstream of the separation unit 28 (or at the bottom of the separation unit, provided that the stream is not materially subjected to separation). This is of important significance because it means that the nitrated stream 40 or 46 can now be mixed with the final nitrated product as a disposal route, without affecting the quality of the nitrated product in regard to the non-nitrated aromatic residual species.

In another embodiment, the nitrated stream 40 is subjected to separation in the secondary separation unit 50 without removal of the acid phase. The aromatic product stream with spent acids is then sent to any location within or downstream of the nitration production train, preferably the washing area of the production train.

The flow chart of FIG. 2 illustrates the steps of the method of the invention. Some conventional steps of the nitration process itself are included in the flow chart for clarity, namely nitrating the aromatic reactant, e.g. benzene in the present example (step 100), recovering the excess reactant from the nitrated product stream (step 102), and recycling the non-nitrated reactant (containing the non-aromatic impurities) to the nitration reactor (step 104). In the method of the invention, a slip stream is diverted from the reactant recycle loop (step 106), and this stream is subjected to nitration (step 108). The flow chart illustrates the alternative ways of handling the product stream from this nitration step 108.

In one embodiment, the spent acids from the nitration step 108 are separated from the organic phase (step 110). The spent acids are recycled to the principal nitration reactor or may be discarded (step 112). The organic phase is sent to the nitration production train (step 114) downstream of the separation step 102. As an alternative to step 114, the non-aromatic impurities are removed (step 116) and the aromatic stream is sent to the nitration production train (step 118), or downstream of the separation step 102. The removed non-aromatic impurities are sent outside of the nitration production train (step 120), e.g. for disposal, or alternatively are sent downstream of the separation step 102, blending them into the nitrated aromatic product (step 122).

In an alternative process for dealing with the product stream from the nitration step 108, the stream is sent directly to the separation step 116, to remove the non-aromatic impurities, without first separating out the spent acids. In this embodiment, the aromatic stream from the separation step 116 contains the spent acids and this product stream is then sent to any location in the nitration production train, or downstream of separation step 102 (step 118). The removed non-aromatic impurities are sent outside of the nitration production train (step 120), e.g. for disposal, or alternatively are sent downstream of the separation step 102, blending them into the nitrated aromatic product (step 122).

In a further alternative process for dealing with the product stream from the nitration step 108, the stream is simply sent to the nitration production train (step 124), downstream of the separation step 102.

Throughout the foregoing description and the drawings, specific details have been set forth in order to provide a more thorough understanding to persons skilled in the art. However, well known elements may not have been shown or described in detail to avoid unnecessarily obscuring the disclosure. For example, various conduits and pumps which provide means to convey streams of reactants and products, and various unit operations commonly used in nitration processes, have not been shown. Accordingly, the description and drawings are to be regarded in an illustrative, rather than a restrictive, sense.

As will be apparent to those skilled in the art in the light of the foregoing disclosure, many alterations and modifications are possible in the practice of this invention without departing from the scope thereof. Accordingly, the scope of the invention is to be construed in accordance with the following claims.

The invention claimed is:

1. A method of removing non-aromatic impurities from non-nitrated aromatic reactant in a nitration production process, in which production process an aromatic reactant is nitrated to produce a nitrated aromatic product using a molar excess of the aromatic reactant, and non-nitrated aromatic reactant is recovered from the produced nitrated aromatic product and is recycled for use in the nitration production process, the method comprising the steps of:

(a) diverting all or a portion of the recovered, non-nitrated aromatic reactant to form a stream comprising non-nitrated aromatic reactant with non-aromatic impurities; and (b) subjecting the stream comprising non-nitrated aromatic reactant formed in step (a) to nitration to produce a first stream comprising nitrated aromatic product with non-aromatic impurities.

2. A method according to claim 1, wherein the first stream comprising nitrated aromatic product produced in step (b) is conveyed to the nitration production process downstream of the separation of non-nitrated aromatic reactant in the nitration production process.

3. A method according to claim 1, wherein the first stream comprising nitrated aromatic product produced in step (b) contains a spent acid phase, and the method further comprises separating the spent acid phase from the nitrated aromatic product to produce a stream comprising spent acids and a second stream comprising nitrated aromatic product with non-aromatic impurities.

4. A method according to claim 3, wherein the separated spent acid phase is recycled for use in the nitration production process.

5. A method according to claim 3, wherein the separated spent acid phase is discarded.

6. A method according to claim 3, further comprising the step of conveying the second stream comprising nitrated aromatic product with non-aromatic impurities to the nitration production process downstream of the separation of non-nitrated aromatic reactant in the nitration production process.

7. A method according to claim 3, further comprising the step of removing the non-aromatic impurities from the second stream comprising nitrated aromatic product with non-aromatic impurities to produce a stream comprising removed non-aromatic impurities and a third stream comprising nitrated aromatic product.

8. A method according to claim 7, wherein the third stream comprising nitrated aromatic product is conveyed to any location within the nitration production process or downstream of the separation of non-nitrated aromatic reactant in the nitration production process.

9. A method according to claim 8, wherein the stream comprising non-aromatic impurities is sent for disposal outside of the nitration production process.

10. A method according to claim 8, wherein the stream comprising non-aromatic impurities is conveyed to the nitration production process downstream of the separation of non-nitrated aromatic reactant in the nitration production process.

11. A method according to claim 1, further comprising the step of removing the non-aromatic impurities from the first stream comprising nitrated aromatic product with non-aromatic impurities to produce a stream comprising removed non-aromatic impurities and a stream comprising nitrated aromatic product.

12. A method according to claim 11, wherein the produced stream comprising nitrated aromatic product is conveyed to any location within the nitration production process or downstream of the separation of non-nitrated aromatic reactant in the nitration production process.

13. A method according to claim 11, wherein the stream comprising non-aromatic impurities is sent for disposal outside of the nitration production process.

14. A method according to claim 11, wherein the stream comprising non-aromatic impurities is conveyed to the nitration production process downstream of the separation of non-nitrated aromatic reactant in the nitration production process.

15. A method according to claim 1, wherein the stream formed in step (a) is a slip stream diverted from a non-nitrated aromatic reactant recycling loop in the nitration production process.

16. A method according to claim 1, wherein step (b) is done with nitric acid, in the presence of sulfuric acid, to produce the nitrated aromatic product.

17. A method according to claim 16, wherein the nitric acid and sulfuric acid are conveyed from the nitration production process.

18. A method according to claim 1, wherein the relative volatility between the nitrated aromatic product and the non-aromatic impurities is higher than between the aromatic reactant and the non-aromatic impurities.

19. A method according to claim 1, wherein the aromatic reactant is one of toluene, benzene, chlorobenzene, or nitrotoluene.

20. A method according to claim 1, wherein the aromatic reactant is benzene and the nitrated aromatic product is mononitrobenzene.

* * * * *